(12) United States Patent
Houser

(10) Patent No.: US 6,971,996 B2
(45) Date of Patent: Dec. 6, 2005

(54) POWER PACKS FOR USE WITH BICENTRIC HINGES

(75) Inventor: Guy M. Houser, Bainbridge Island, WA (US)

(73) Assignee: Thuasne, Levallois Perret (FR)

( * ) Notice: Subject to any disclaimer, the term of this patent is extended or adjusted under 35 U.S.C. 154(b) by 0 days.

(21) Appl. No.: 10/879,399

(22) Filed: Jun. 29, 2004

(65) Prior Publication Data

US 2004/0267176 A1 Dec. 30, 2004

Related U.S. Application Data

(60) Provisional application No. 60/484,074, filed on Jun. 30, 2003.

(51) Int. Cl.[7] .............................................. A61F 5/00
(52) U.S. Cl. ........................... 602/16; 602/26; 602/62; 128/882; 128/898; 16/54
(58) Field of Search ................................ 602/16, 5, 23, 602/26, 60, 61, 62; 128/99.1, 103.1, 123.1, 128/845, 869, 882, 898; 623/39; 482/111, 482/112, 113; 16/54

(56) References Cited

U.S. PATENT DOCUMENTS

| | | | | |
|---|---|---|---|---|
| 3,528,412 A | * | 9/1970 | McDavid | 602/16 |
| 3,799,158 A | * | 3/1974 | Gardner | 602/16 |
| 5,356,370 A | * | 10/1994 | Fleming | 602/16 |
| 5,472,412 A | * | 12/1995 | Knoth | 602/26 |
| 5,782,785 A | * | 7/1998 | Herzberg | 602/26 |
| 5,885,235 A | * | 3/1999 | Opahle et al. | 602/16 |
| 6,314,612 B1 | * | 11/2001 | Rennecke et al. | 16/54 |
| 6,413,232 B1 | * | 7/2002 | Townsend et al. | 602/16 |
| 6,527,733 B1 | * | 3/2003 | Ceriani et al. | 602/16 |
| 6,540,709 B1 | * | 4/2003 | Smits | 602/16 |
| 6,875,187 B2 | * | 4/2005 | Castillo | 602/5 |
| 6,878,126 B2 | * | 4/2005 | Nelson et al. | 602/26 |

* cited by examiner

Primary Examiner—Fadi H. Dahbour
(74) Attorney, Agent, or Firm—Perkins Coie LLP

(57) ABSTRACT

Power packs for use with bicentric hinges and methods for operating hinges are disclosed herein. In one embodiment of the invention, a power pack has a housing with a cavity and a piston disposed at least partially within the cavity. The housing has an attachment mechanism configured to attach the housing to a hinge. The piston has a head and an arm configured to be connected to the head and one of the hinge members. In one embodiment, the head is moveable about a first axis of rotation along a circular path through the cavity. An embodiment for operating the hinge includes rotating the first hinge member coupled to the piston about the first axis of rotation, displacing a fluid from the cavity to a fluid passageway as the piston rotates, and pivoting the second hinge member about a second axis of rotation.

22 Claims, 14 Drawing Sheets

POWER PACKS FOR USE WITH BICENTRIC HINGES

RELATED APPLICATIONS

This application claims the benefit of provisional U.S. patent application No. 60/484,074, filed Jun. 30, 2003, which is hereby incorporated by reference in its entirety.

TECHNICAL FIELD

The present invention relates to power packs for use with bicentric hinges.

BACKGROUND

Knee braces are widely used to stabilize and protect the knee joint. For example, knee braces are often used to prevent damage to the anterior cruciate ligament, posterior cruciate ligament, medial collateral ligament, lateral collateral ligament and/or miniscus in a knee joint. Knee braces are particularly useful to protect the knee joint during vigorous athletic activities such as running, basketball, football and skiing, and they are also used to stabilize the knee joint during recovery or rehabilitation from surgery or an injury.

A knee brace typically includes an upper frame, a lower frame, and a hinge connecting the upper frame to the lower frame. The upper frame often has straps that wrap around the quadriceps or hamstring, and the lower frame often has straps that wrap around the calf. Each portion of the frame is configured to fit the shape of the corresponding portion of the leg. The hinge allows the lower frame to pivot relative to the upper frame as the knee bends. Many braces have a hinge on each side of the knee joint to give the brace additional strength.

Conventional hinges for knee braces include a single axis pivot, two gears or a four-bar linkage. The conventional geared hinge mechanisms typically have two rotating gears with interlocking teeth. The single axis pivot and geared hinge mechanisms have several disadvantages. First, the single axis pivot and geared hinge mechanisms limit the range of flexion of the leg. Second, the single axis pivot and geared hinges do not simulate the natural movement of the knee joint when the leg bends or extends. The motion of the human knee joint is quite complex and does not rotate uniformly from extension to flexion. Because the single axis pivot and geared hinge mechanisms cannot simulate the natural movement of the knee joint, the knee brace may force the knee into an unnatural position at extension or flexion if the straps on the knee brace are tight. This coupled with forces induced during activity may injure the knee joint. Moreover, a user may loosen the straps to avoid the discomfort resulting from the unnatural movement of the knee joint. If the straps on the knee brace are loose, however, the knee brace will slide down the leg during an activity. Such movement of the knee brace during an activity is uncomfortable and annoying. Additionally, as the knee brace slides down the leg, the straps might not be tight enough to provide the necessary support to the knee. Third, the single axis pivot and geared hinge mechanisms require a certain amount of disassembly in order to adjust the stops that limit the range of motion of the knee brace. Some single axis pivot and geared hinge mechanisms do not even allow the range of motion stops to be adjusted. Others allow the stops to be adjusted but only to a limited number of positions. Moreover, range of motion stops in single axis pivot and geared hinge mechanisms can stop rotation of the hinge abruptly, causing hyperextension of a ligament in the knee or high loads in the knee joint and knee brace.

A four-bar linkage hinge mechanism better simulates the motion of the knee during flexion and extension than single axis pivot and geared hinges. Four-bar linkage hinges, however, have several disadvantages. First, the motion of a four-bar linkage hinge is complex, making it difficult to set and adjust the stops that limit the range of motion of the knee brace. As a result, patients may not accurately limit the range of motion with four-bar linkage hinge mechanisms. Second, four-bar linkage hinges are bigger than many other types of hinges. A big knee brace hinge can make it more difficult to pull clothes over the brace, and large hinges may interfere with the other knee joint during activities. Therefore, four-bar linkage hinges are not widely used in knee braces. Third, the four-bar linkage hinge also requires a certain amount of disassembly in order to adjust the stops that limit the range of motion of the knee brace. Moreover, the range of motion stops in the four-bar linkage hinge also can stop rotation of the hinge abruptly, causing hyperextension of a ligament in the knee, or high loads in the knee joint and knee brace.

SUMMARY

The present invention is directed toward power packs for use with bicentric hinges and methods for operating hinges. In one embodiment of the invention, a power pack has a housing with a cavity and a piston disposed at least partially within the cavity. The piston is generally a rotary piston in several embodiments, but the piston can move along a linear axis in other embodiments. The housing has an attachment mechanism configured to attach the housing to a hinge. The piston has a head and an arm configured to be connected to the head and one of the hinge members. In one embodiment, the head is moveable about a first axis of rotation along a circular path through the cavity.

An embodiment for operating the hinge includes rotating the first hinge member coupled to the piston about the first axis of rotation. The rotation of the hinge member drives the piston through the cavity, which displaces a fluid from the cavity to a fluid passageway. This particular embodiment can also include pivoting the second hinge member about a second axis of rotation. The second hinge member can be coupled to a second piston to drive the additional fluid from a second cavity in a similar manner in another embodiment.

DETAILED DESCRIPTION

The following disclosure describes several embodiments of power packs for use with bicentric hinges and methods for operating hinges. Many specific details of certain embodiments of the invention are set forth in the following description and in FIGS. 1–11 to provide a thorough understanding of such embodiments. One skilled in the art, however, will understand that the invention may have additional embodiments or that the invention may be practiced without several of the details described in the following description. For example, even though many embodiments of the power pack are described with reference to a knee brace hinge, they can also be used in elbow braces or other braces.

Figure 1:
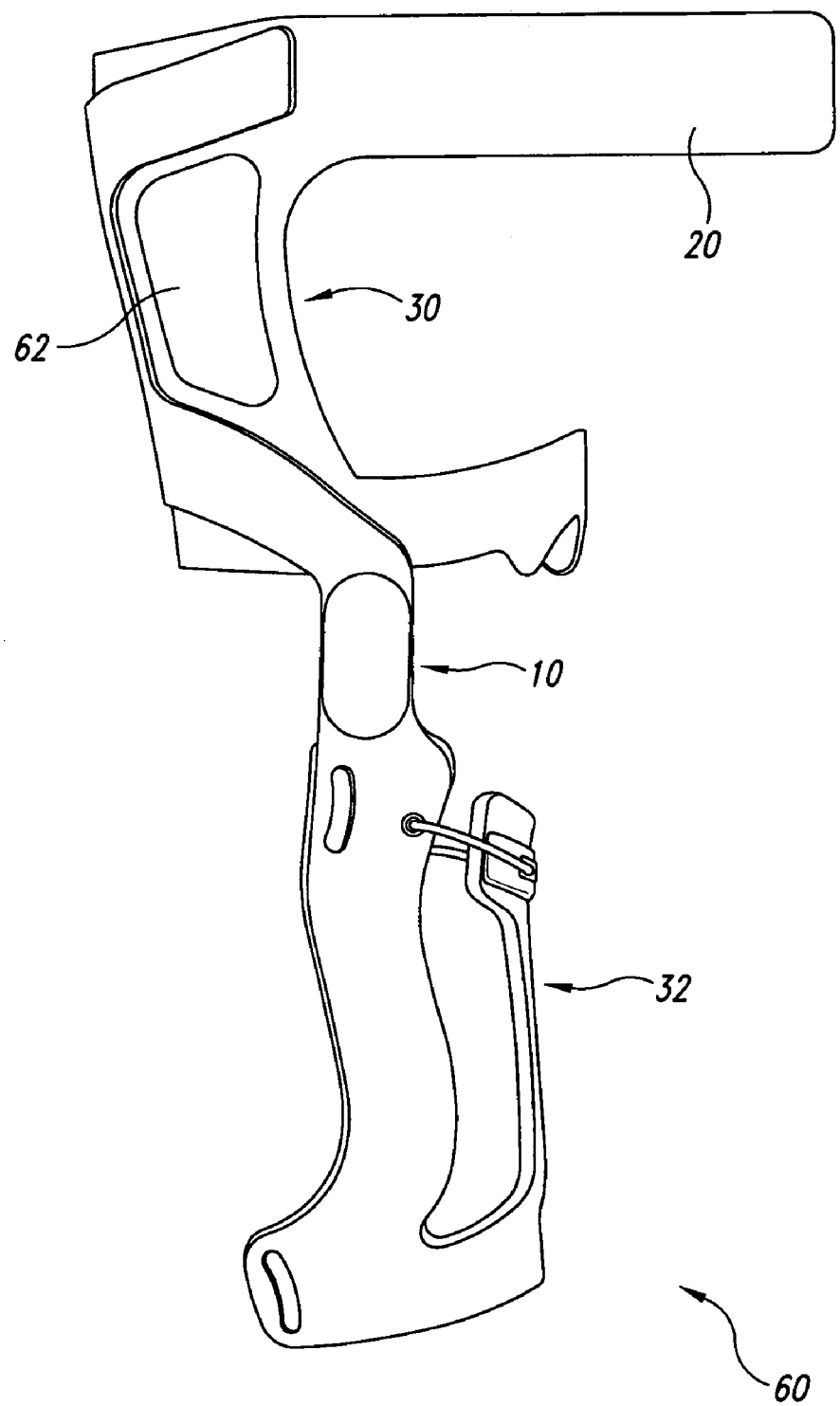
FIG. 1 is a side view of a knee brace with a hinge in accordance with one embodiment of the invention.

FIG. 1 is a side view of a knee brace 60 including an upper frame 30, a lower frame 32, and hinges 10 connecting the upper frame 30 to the lower frame 32. The upper frame 30 can include at least one strap 20 to wrap around the quadriceps or hamstring, and the lower frame 32 can also include one or more straps. In other embodiments, the upper and lower frames 30 and 32 can have different configurations and include different configurations of straps. For example, the knee brace 60 can also include a flexible, elastic sleeve 62 coupled either directly or indirectly to the upper and lower frames 30 and 32.

Figure 2:
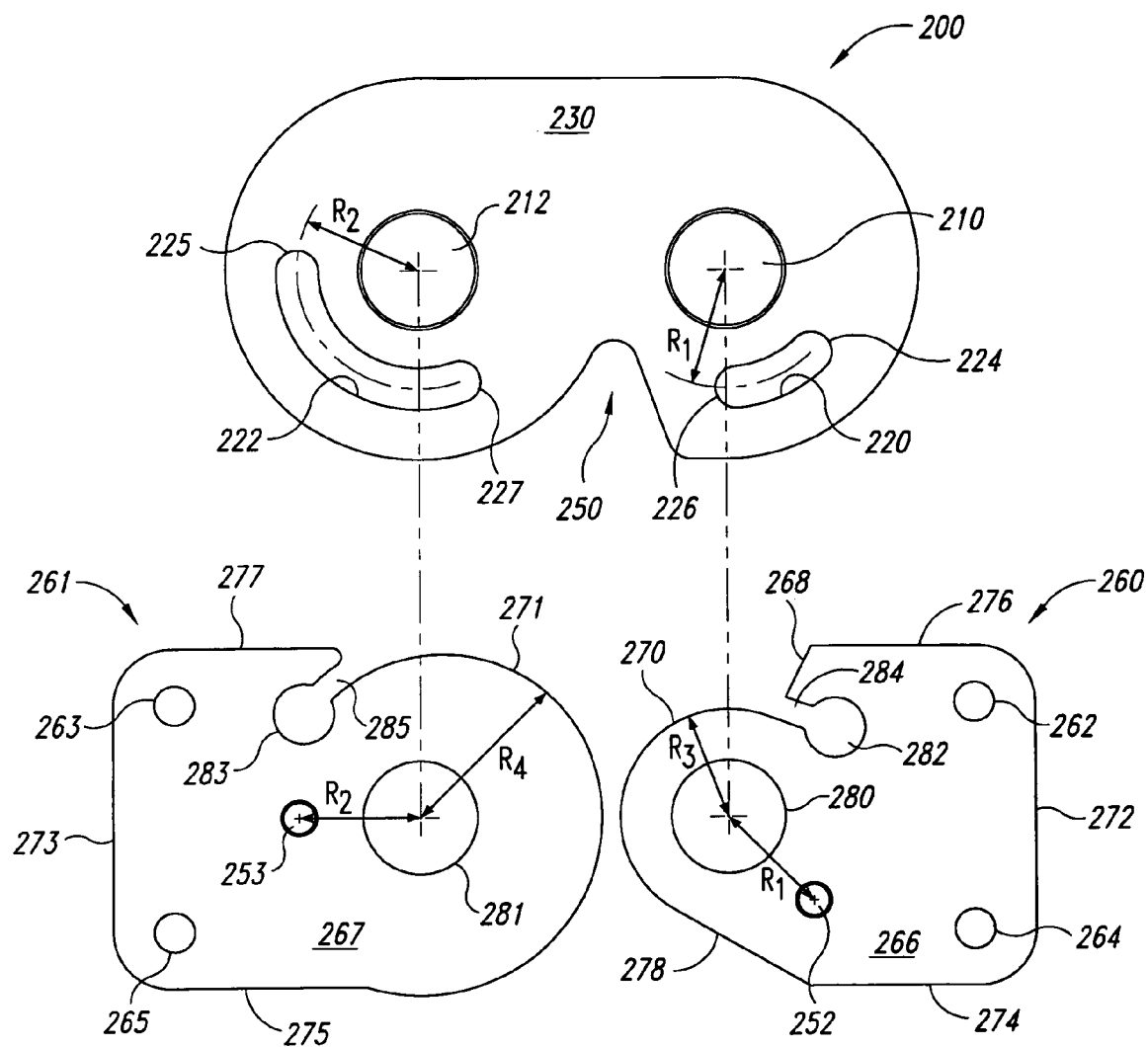
FIG. 2 is an exploded view of a plate, a first hinge member, and a second hinge member of the hinge of FIG. 1.
Figure 3A:
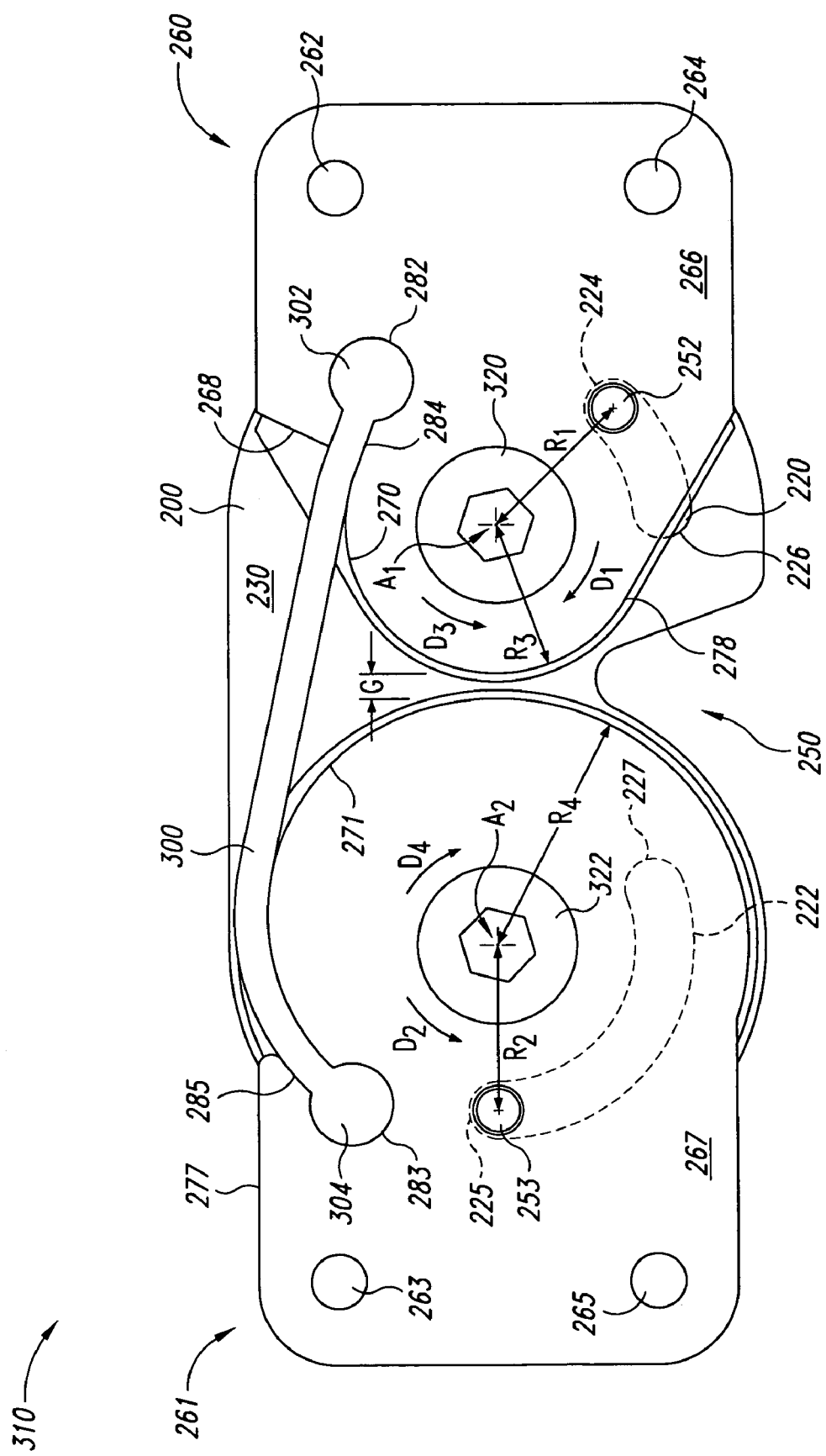
FIG. 3A is a top plan view of an assembly including a resilient member with the plate, the first hinge member, and the second hinge member of FIG. 2.

FIG. 2 is an exploded view and FIG. 3A is a top plan view of one embodiment of the hinge 10. In this embodiment, the hinge 10 includes a back plate 200, a first hinge member 260, and a second hinge member 261. The first hinge member 260 rotatably mounts to the back plate 200 and is configured to attach to the upper frame 30 (FIG. 1) to permit the upper frame 30 to pivot relative to the back plate 200. The second hinge member 261 also rotatably mounts to the back plate 200 and is configured to attach to the lower frame 32 (FIG. 1) to permit the lower frame 32 to pivot relative to the back plate 200 independently of the upper frame 30. Accordingly, the upper and lower frames 30 and 32 pivot independently about two different axes of rotation.

Referring to FIG. 2, the first hinge member 260 is a generally flat plate with a front surface 266 and a back surface (not shown) opposite the front surface 266. Between the front surface 266 and the back surface are a top edge 276, a bottom edge 274 and a side edge 272 configured for attachment to a portion of the upper frame 30. For example, the first hinge member 260 can include two apertures 262 and 264 proximate the side edge 272 for receiving fasteners (not shown) to connect the upper frame 30 to the first hinge member 260. The second hinge member 261, similarly, has a front surface 267 and a back surface (not shown) opposite the front surface 267. Between the front surface 267 and the back surface are a top edge 277, a bottom edge 275 and a side edge 273 configured for attachment to a portion of the lower frame 32. The second hinge member 261 can also include two apertures 263 and 265 proximate the side edge 273 for receiving fasteners (not shown) to connect the lower frame 32 to the second hinge member 261. In additional embodiments, the first hinge member 260 can be an integral portion of the upper frame 30 and the second hinge member 261 can be an integral portion of the lower frame 32. The first and second hinge members 260 and 261 can have different configurations in other embodiments.

Referring to FIGS. 2 and 3A together, the first hinge member 260 is pivotally connected to the back plate 200 by a fastener 320. The first hinge member 260 rotates relative to the back plate 200 about a first axis of rotation $A_1$ (FIG. 3A). The first hinge member 260 has a pin 252 that projects from the front surface 266 and the back surface. In additional embodiments, the pin 252 can have a different configuration or shape. For example, the pin 252 can extend or project from either the front surface 266 or the back surface. The portion of the pin 252 projecting from the back surface is received within an annular slot 220 in the back plate 200. The annular slot 220 is accordingly centered about the first axis of rotation $A_1$ with a centerline at a radius $R_1$ corresponding to the distance from the first axis of rotation $A_1$ to the pin 252. Accordingly, as the first hinge member 260 rotates relative to the back plate 200 about the first axis of rotation $A_1$, the pin 252 slides in the annular slot 220. A first endpoint 224 and a second endpoint 226 of the slot 220 define the maximum range of motion for the first hinge member 260. Accordingly, the length of the slot 220 determines the pivoting range of the first hinge member 260 relative to the back plate 200. In additional embodiments, the slot 220 can have different lengths to change the pivoting range of the first hinge member 260. In other embodiments, the position of the slot 220 and the pin 252 can be different, such as the slot 220 can be in the first hinge member 260 and the pin 252 can be attached to the back plate 200.

The second hinge member 261 is pivotally connected to the back plate 200 by a fastener 322. The second hinge member 261 rotates relative to the back plate 200 about a second axis of rotation $A_2$ (FIG. 3A). The second hinge member 261 has a pin 253 that projects from the front surface 267 and the back surface. In additional embodiments, the pin 253 can have a different configuration or shape. For example, the pin 253 can extend or project from either the front surface 267 or the back surface, or there can be two separate pins with one extending from each surface. The portion of the pin 253 projecting from the back surface is received within an annular slot 222 in the back plate 200. The annular slot 222 is accordingly centered about the second axis of rotation $A_2$ with a centerline at a radius $R_2$ corresponding to the distance from the second axis of rotation $A_2$ to the pin 253. As the second hinge member 261 rotates relative to the back plate 200 about the second axis of rotation $A_2$, the pin 253 slides in the annular slot 222. A first endpoint 225 and a second endpoint 227 of the slot 222 define the maximum range of motion for the second hinge member 261. The length of the slot 222 determines the pivoting range of the second hinge member 261 relative to the back plate 200. In additional embodiments, the slot 222 can have a different length to change the pivoting range of the second hinge member 261. In other embodiments, the position of the slot 222 and the pin 253 can be different, such as the slot 222 can be in the second hinge member 261 and the pin 253 can be attached to the back plate 200.

Referring to FIG. 3A, the curved edge 270 on the first hinge member 260 is spaced away from the curved edge 271 on the second hinge member by a gap G. Accordingly, the first hinge member 260 and the second hinge member 261 pivot independently about the two different axes of rotation $A_1$ and $A_2$. Because the hinge has two different and independent axes of rotation, it better simulates the natural motion of the knee joint. This is expected to mitigate the sliding of the knee brace down the leg and reduce the exertion of unnatural forces against the knee joint.

In the illustrated embodiment, the back plate 200 has a cutout portion 250. The cutout portion 250 allows the first and second hinge members 260 and 261 to rotate through the full pivoting range without the upper and lower frames 30 and 32 (FIG. 1) striking the back plate 200.

In the illustrated embodiment, the first hinge member 260 and the second hinge member 261 are operatively coupled by a resilient member 300. The resilient member 300 has a first end 302 attached to the first hinge member 260 and a second end 304 attached to the second hinge member 261. The first end 302 is received within an aperture 282 in the first hinge member 260. A channel 284 connects the aperture 282 to an edge 268 and is sized to receive a portion of the resilient member 300. Similarly, the second end 304 of the resilient member 300 is received within an aperture 283 of the second hinge member 261. A channel 285 connects the aperture 283 to the edge 277 and is sized to receive a portion of the resilient member 300. The first end 302 and the second end 304 of the resilient member 300 are enlarged so that they are not pulled through the smaller channels 284 and 285. In one embodiment, the first end 302 and the second end 304 of the resilient member 300 have a donut shape with a pin in the center. In other embodiments, the first end 302 and second end 304 of the resilient member 300 can be clamped or bonded.

The resilient member 300 is elastic and provides resistance to the hinge members 260 and 261 during flexion. In one embodiment, urethane can be used; in other embodiments other materials may be used. The resilient member 300 stretches as the first hinge member 260 rotates in a direction $D_1$ and/or the second hinge member 261 rotates in a direction $D_2$. The resilient member 300 urges the first hinge member 260 to rotate in a direction $D_3$ and the second hinge member 261 to rotate in a direction $D_4$. Accordingly, when no external force is placed on the first and second hinge members 260 and 261, the pins 252 and 253 are drawn toward the first endpoints 224 and 225 of the slots 220 and 222. When an external force is applied to the first hinge member 260 causing rotation in the direction $D_1$, the resilient member 300 stretches elastically and rides along a curved edge 270 of the first hinge member 260. In the illustrated embodiment, the curved edge 270 has a radius $R_3$. In one embodiment, the curved edge 270 may not have a constant radius. Similarly, when an external force is applied to the second hinge member 261 causing rotation in the direction $D_2$, the resilient member 300 stretches elastically and rides along a curved edge 271 of the second hinge member 261. In the illustrated embodiment, the curved edge 271 has a radius $R_4$ that is greater than the radius $R_3$. In additional embodiments, the radius $R_3$ can be equal to or greater than the radius $R_4$.

The resilient member 300 and the radii of the hinge members 260 and 261 operate together to control the rotation of the hinge members 260 and 261. For example, when $R_3$ is less than $R_4$, the first hinge member 260 rotates in direction $D_1$ for an arc length before the second hinge member 261 rotates in direction $D_2$ for an arc length. This is because a greater external force must be applied to rotate a member with a greater radius in light of the counter force applied by the resilient member 300. Accordingly, in the illustrated embodiment, when an external force is applied to the hinge 310, the first hinge member 260 rotates first because its radius $R_3$ is less than the radius $R_4$ of the second hinge member 261. The second hinge member 261 will begin to rotate after the pin 252 of the first hinge member 260 has rotated through at least a portion of its range of motion. The rotation of one hinge member before the rotation of the other hinge member simulates the natural anatomical motion of the knee joint during extension and flexion. A better simulation of the natural motion of the knee joint reduces the movement of the knee brace down the leg of the user and the tendency of the knee brace to force the knee into unnatural positions.

Figure 3B:
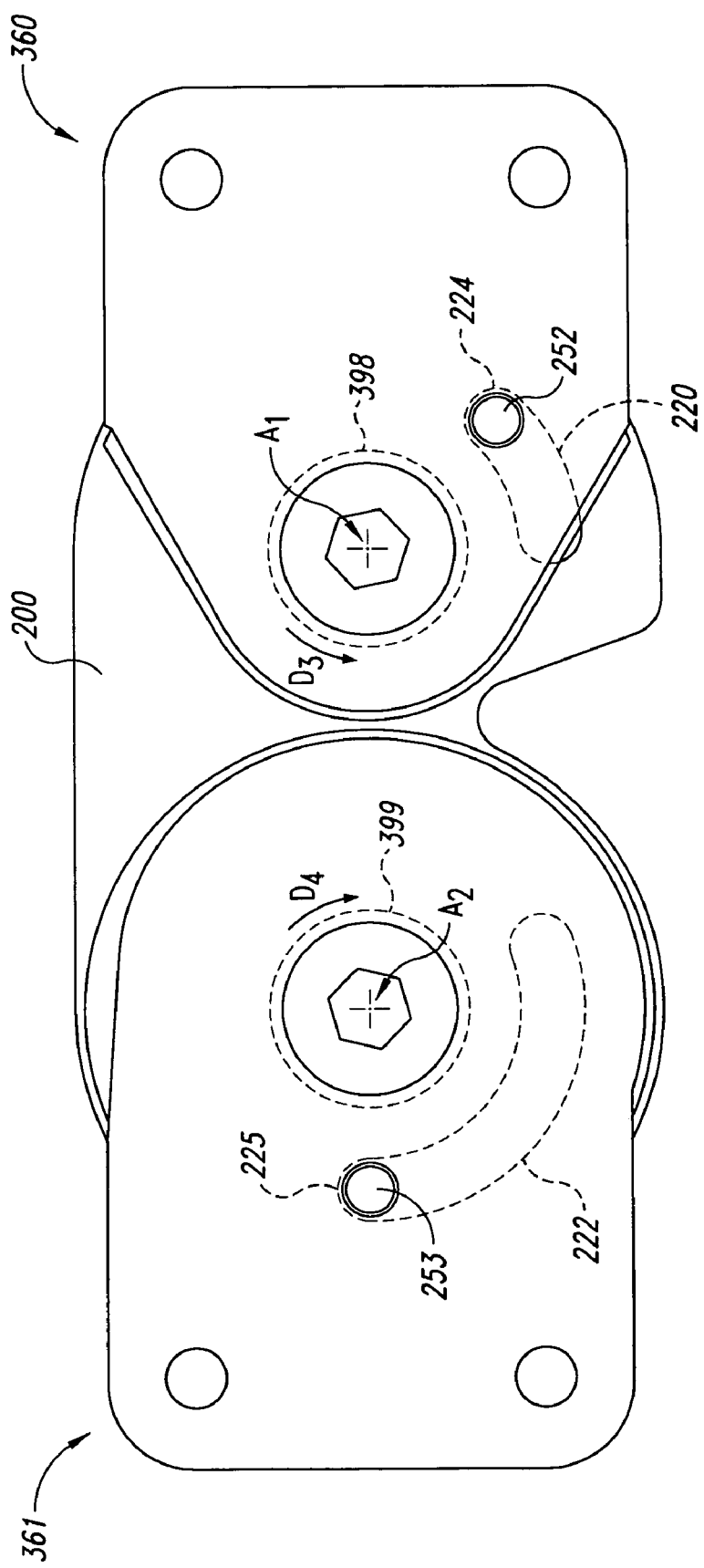
FIG. 3B is a top plan view of an assembly including a first torsion spring attached to a first hinge member and a second torsion spring attached to a second hinge member in accordance with another embodiment of the invention.

FIG. 3B is a top plan view of an assembly including a first torsion spring 398 attached to a first hinge member 360 and a second torsion spring 399 attached to a second hinge member 361 in accordance with another embodiment of the invention. Each torsion spring 398 and 399 is also attached to the back plate 200. The first torsion spring 398 urges the first hinge member 360 to rotate in the direction $D_3$ and the second torsion spring 399 urges the second hinge member to rotate in the direction $D_4$. Accordingly, when no external force is placed on the first and second hinge members 360 and 361, the pins 252 and 253 are drawn toward the first endpoints 224 and 225 of the slots 220 and 222. In one embodiment, the torsion springs can have different spring coefficients causing one hinge member to rotate before the other.

Figure 4:
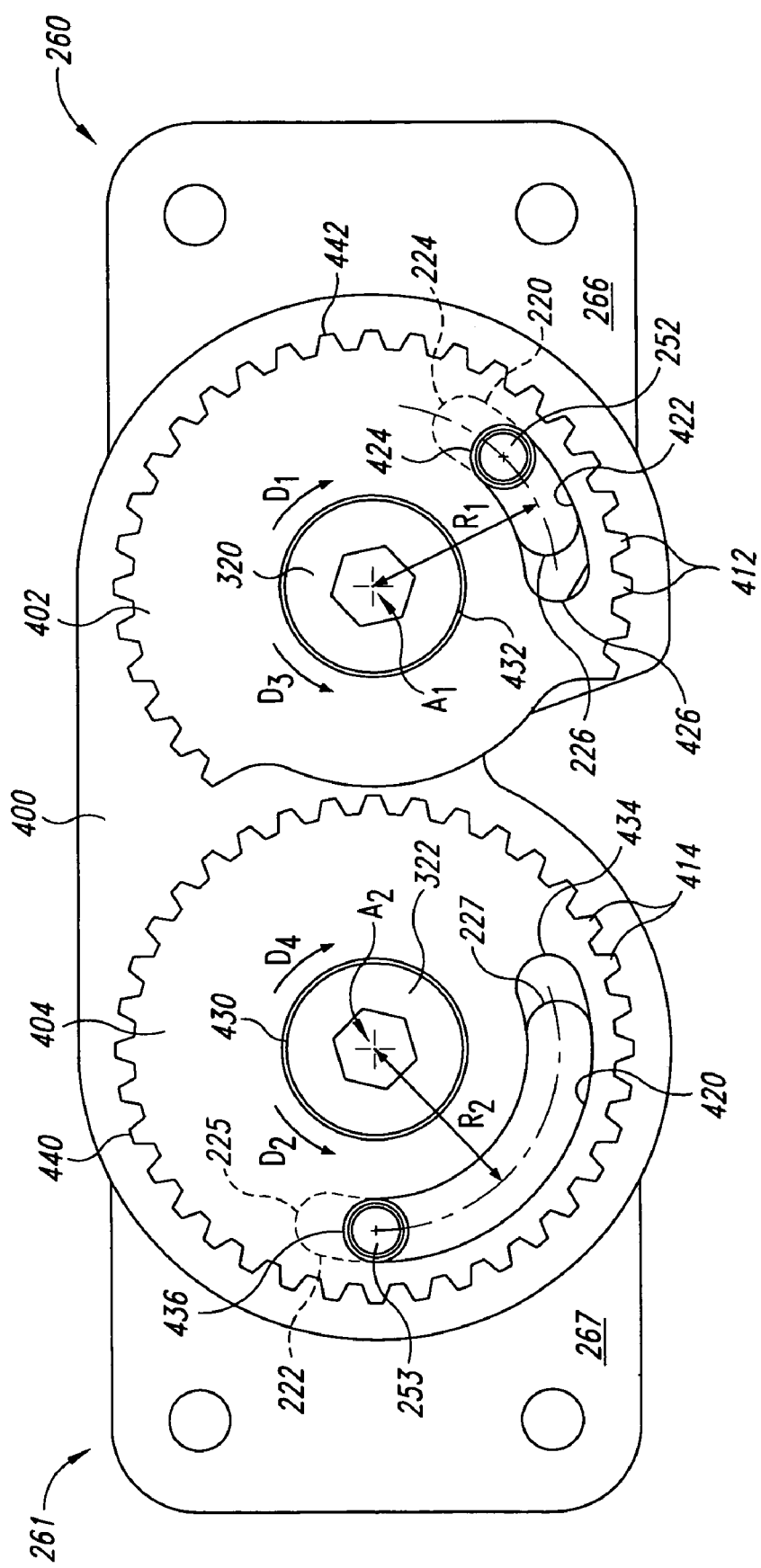
FIG. 4 is a top plan view of first and second adjustable range restrictors.
Figure 5B:
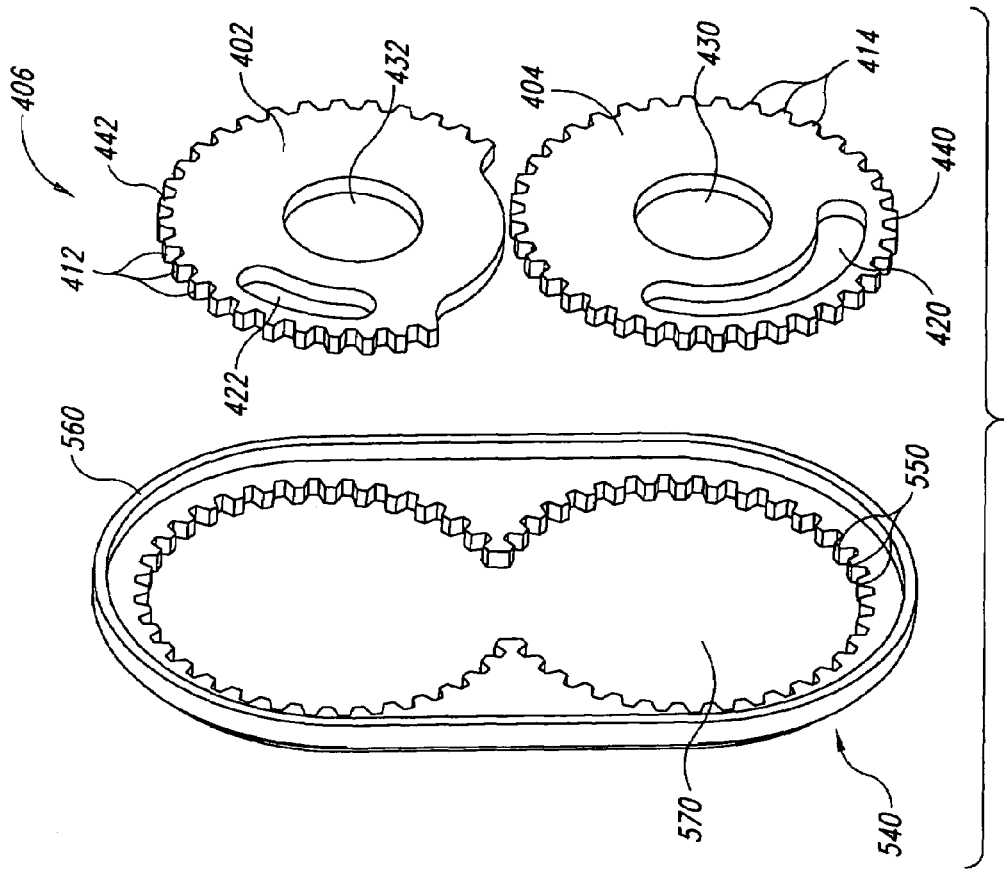
FIG. 5B is an isometric view of the adjustable range restrictor system of FIG. 5A with the first and second adjustable range restrictors removed from a cover plate.
Figure 5A:
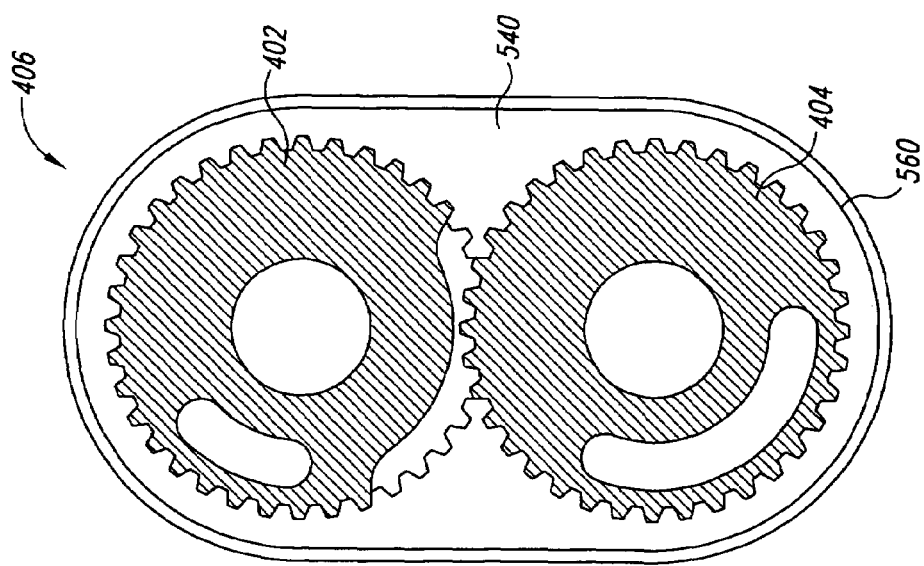
FIG. 5A is a top plan view of an adjustable range restrictor system in accordance with one embodiment of the invention.

FIG. 4 is a top plan view of the hinge 310 of FIG. 3A with first and second adjustable range restrictors 402 and 404. FIG. 5A is a top plan view of an adjustable range restrictor system 406 in accordance with one embodiment of the invention. FIG. 5B is an isometric view of the adjustable range restrictor system 406 of FIG. 5A with the first and second adjustable range restrictors 402 and 404 removed from a housing 540. As explained in more detail below, the adjustable range restrictor system 406 allows a user to adjust the pivoting range of the first hinge member 260 and/or the second hinge member 261.

Referring to the illustrated embodiment in FIG. 4, the fastener 320 is received in an aperture 432 of the first adjustable range restrictor 402 so that the first adjustable range restrictor 402 is positionable about the first axis of rotation $A_1$. The first adjustable range restrictor 402 has an annular slot 422 extending about the first axis of rotation $A_1$ with a centerline at the radius $R_1$. The slot 422 is positioned and sized to receive the pin 252 of the first hinge member 260. Accordingly, when the first hinge member 260 pivots, the pin 252 moves within the slot 422. Similarly, the fastener 322 is received in an aperture 430 of the second adjustable range restrictor 404 so that the second adjustable range restrictor 404 is positionable about the second axis of rotation $A_2$. The second adjustable range restrictor 404 has an annular slot 420 extending about the second axis of rotation $A_2$ with a centerline at the radius $R_2$. The slot 420 is positioned and sized to receive the pin 253 of the second hinge member 261. Accordingly, when the second hinge member 261 pivots, the pin 253 moves within the slot 420. In the illustrated embodiment, the length of the slot 420 is approximately equal to the length of the slot 222, and the length of the slot 422 is approximately equal to the length of the slot 220. In other embodiments, the slots 420 and 422 can have different lengths.

The first and second adjustable range restrictors 402 and 404 can be rotated so that their slots 422 and 420 limit the rotation of the first and second hinge members 260 and 261. For example, referring to the embodiment in FIG. 4, the first adjustable range restrictor 402 is positioned so that the slot 422 is offset from the slot 220 of the first hinge member 260. Consequently, a first endpoint 424 of the slot 422 and the second endpoint 226 of the slot 220 define stops for the pin 252 to limit the rotation of the first hinge member 260 about the first axis of rotation $A_1$. The first adjustable range restrictor 402 can be rotated further in the direction $D_1$ to further limit the rotation of the first hinge member 260. Conversely, the first adjustable range restrictor 402 can be rotated in the direction $D_3$ to increase the range of rotation. The second adjustable range restrictor 404 can similarly be positioned about the second axis of rotation $A_2$ so that the slot 420 is offset from the slot 222 to define stops for the pin 253 that limit the rotation of the second hinge member 261 about the second axis of rotation $A_2$.

The adjustable range restrictors 402 and 404 are held in place by the housing 540. Referring to FIGS. 5A and 5B, at least a portion of the outer edge 442 of the first adjustable range restrictor 402 has teeth 412, and the outer edge 440 of the second adjustable range restrictor 404 also has teeth 414. The housing 540 has a recess 570 with teeth 550 that engage the teeth 412 and 414 of the first and second adjustable range restrictors 402 and 404. When the housing 540 is attached to a front plate 400 (FIG. 4), the teeth 550 preclude the first and second adjustable range restrictors 402 and 404 from rotating about the first and second axes of rotation $A_1$ and $A_2$. The housing 540, for example, can have a lip 560 that snap-fits onto the front plate 400 to lock the first and second range restrictors 402 and 404 in the desired positions for limiting the range of motion. The first and second adjustable range restrictors 402 and 404 are rotatably adjusted by removing the housing 540, rotating the first and second adjustable range restrictors 402 and 404, and replacing the housing 540. The configuration of the teeth 412, 414 and 550 in the illustrated embodiment permits the first and second adjustable range restrictors 402 and 404 to be adjusted in 10-degree increments. In additional embodiments, the teeth 412, 414 and 550 can be sized and spaced differently.

One advantage of the embodiment of the range restrictor system 406 shown in FIGS. 4–5B is the ease with which a user can adjust the pivoting range of the first and second hinge members 260 and 261. It will be appreciated that the range restrictor system 406 can have other configurations. For example, in additional embodiments, other types of devices can be used to restrict the first and second adjustable range restrictors 402 and 404 from rotating about the first and second axes of rotation $A_1$ and $A_2$. In one such embodiment, the front plate 400 could have a projection with teeth that engage the teeth of one or both of the adjustable range restrictors 402 and 404, thus eliminating the need for the housing 540. In the illustrated embodiment, the front plate 400 is similar to the back plate 200, but is positioned on the other side of the hinge members 260 and 261. In still other embodiments, the front plate 400 can have a different configuration, or the hinge may not have the front plate 400. In further embodiments, the first and second adjustable range restrictors 402 and 404 can be placed proximate to the first and second hinge members 260 and 261, or the adjustable range restrictor system 406 can be placed adjacent to the back surface of the back plate 200. In additional embodiments, the hinge may not have the adjustable range restrictor system 406.

Figure 6:
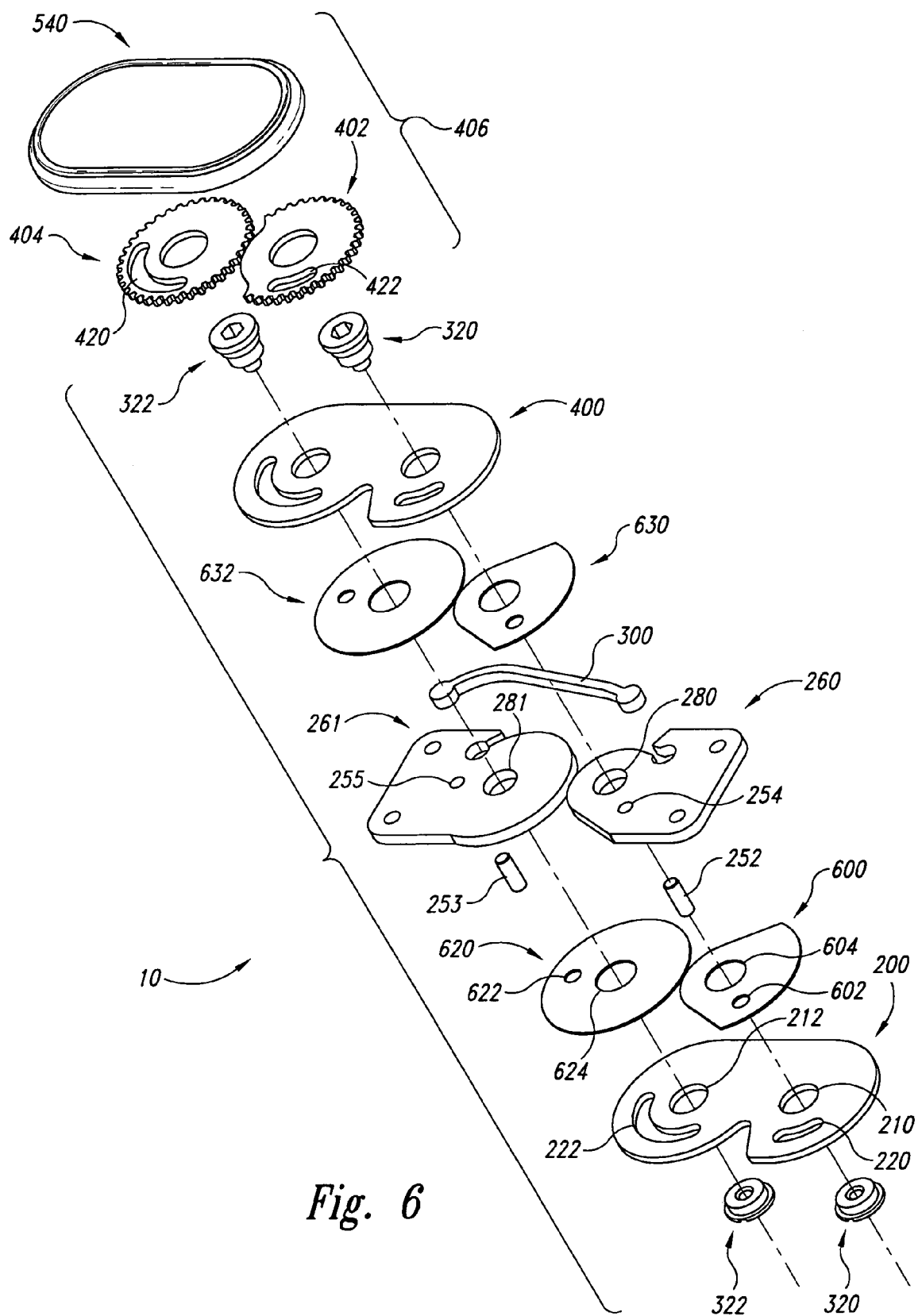
FIG. 6 is an isometric exploded view of a hinge and range restrictor in accordance with an embodiment of the invention.

FIG. 6 is an exploded view of the hinge 10 of FIG. 1. In the illustrated embodiment, the first and second hinge members 260 and 261 are held between the back plate 200 and the front plate 400 by the fasteners 320 and 322. The hinge 10 can have spacers 600, 620, 630 and 632 to assist the first and second hinge members 260 and 261 to rotate more easily between the plates 400 and 200. The spacers 600 and 630 have an aperture 604 through which the fastener 320 is placed, and an aperture 602 through which the first pin 252 is placed. Similarly, the spacers 620 and 632 have an aperture 624 through which the fastener 322 is placed, and an aperture 622 through which the second pin 253 is placed. In additional embodiments, the spacers 600, 620, 630 and 632 can have different configurations, or the hinge 10 may not have one or more of the spacers 600, 620, 630 and 632. The range restrictor system 406 attaches to the front plate 400 as explained above.

FIG. 6 also illustrates the compactness of the hinge 10 and the range restrictor system 406. The hinge 10 and the range restrictor system 406 together can have a thickness of between 0.125 inch and 1 inch. In one embodiment, the hinge 10 and the range restrictor system 406 together have a thickness of approximately 0.31 inch. The compact size of the hinge 10 and the range restrictor system 406 makes it easier to wear clothes over the knee brace and reduces the risk of the hinge interfering with the other knee joint during activities.

Figure 7A:
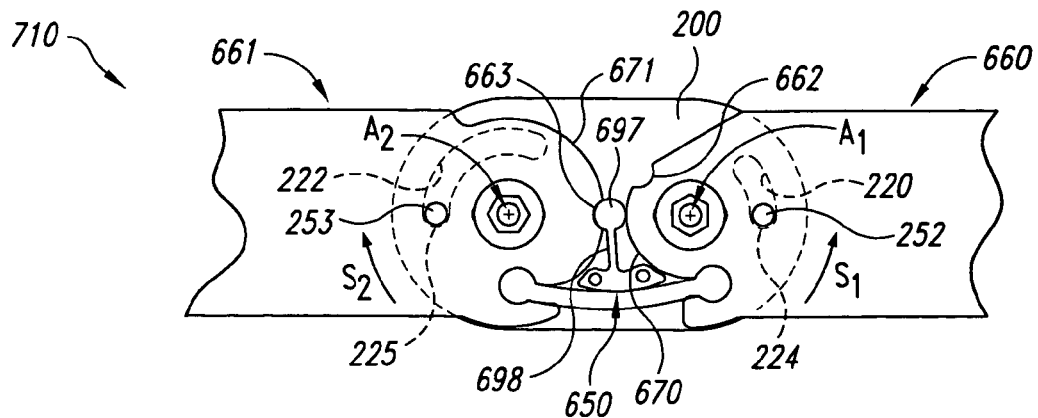
FIGS. 7A–7C are top plan views illustrating a hinge with a rocker in accordance with another embodiment of the invention.
Figure 7B:
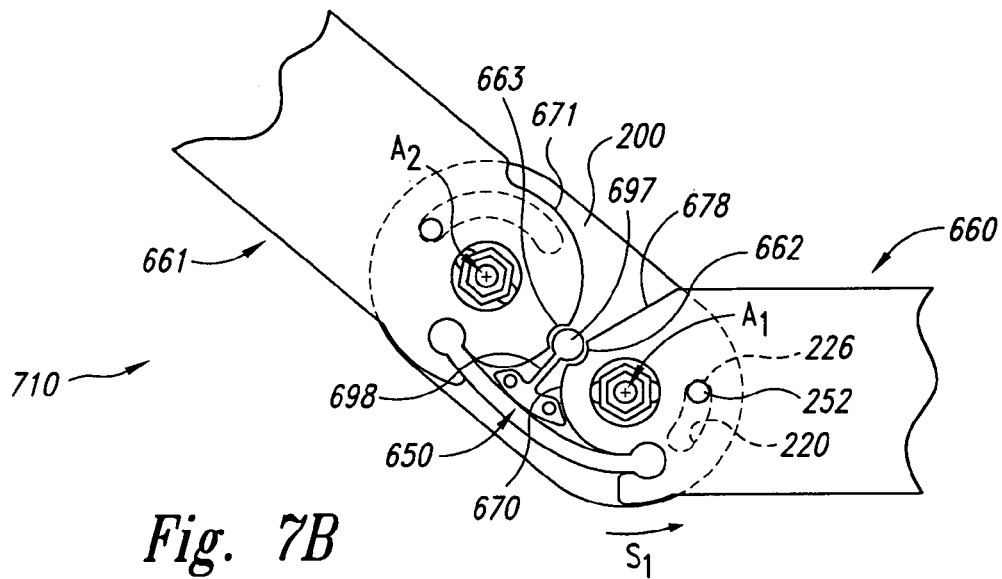
Figure 7C:
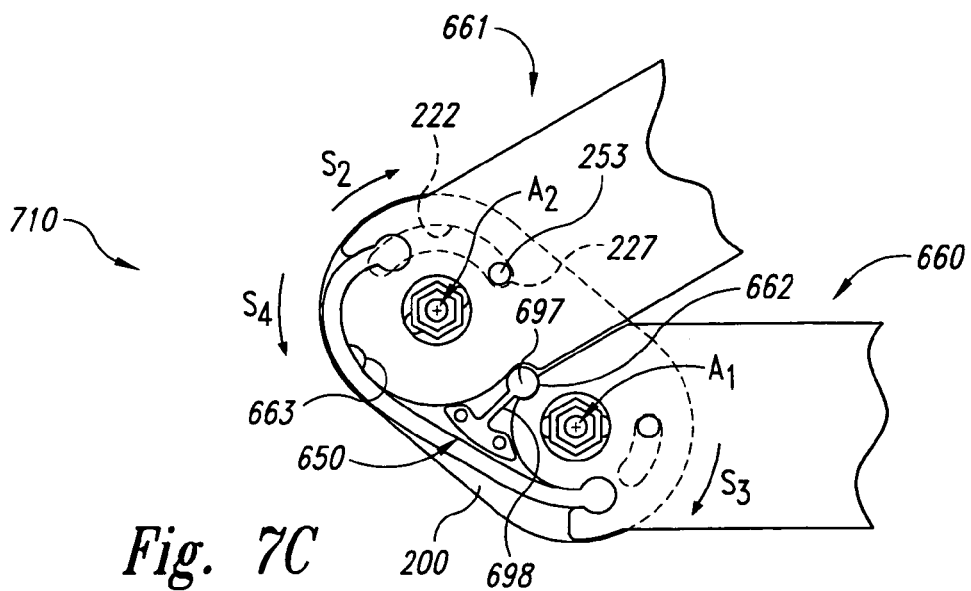

FIGS. 7A–7C are top plan views illustrating a hinge 710 in accordance with another embodiment of the invention. The hinge 710 is similar to the hinge 10 described above, and like reference numbers refer to like components in FIGS. 1–7C. In the illustrated embodiment, the hinge 710 includes a first hinge member 660 with a first recess 662 and a second hinge member 661 with a second recess 663. The first and second hinge members 660 and 661 are pivotally coupled to the back plate 200. Referring to FIG. 7A, the pin 252 of the first hinge member 660 is positioned at the first endpoint 224 of the slot 220 in the back plate 200, and the pin 253 of the second hinge member 661 is positioned at the first endpoint 225 of the slot 222 in the back plate 200. The hinge 710 also includes a rocker 650 attached to the back plate 200. The rocker 650 has a flexible arm 698 and a head 697 positioned between the first hinge member 660 and the second hinge member 661.

When the hinge 710 is in the full-extension position shown in FIG. 7A, the head 697 is proximate a curved edge 670 of the first hinge member 660 and at least partially within the second recess 663 of the second hinge member 661. Because the head 697 of the rocker 650 is at least partially within the second recess 663 of the second hinge member 661, the second hinge member 661 is effectively jammed and restricted from movement. Accordingly, a force applied to either hinge member 660 or 661 will cause the first hinge member 660 to pivot in a direction $S_1$ about the first axis of rotation $A_1$.

Referring to FIG. 7B, the first hinge member 660 has pivoted about the first axis of rotation $A_1$ to a position where the pin 252 is at the second endpoint 226 of the slot 220 in the back plate 200. The first hinge member 660 accordingly cannot pivot further about the first axis of rotation $A_1$ in the direction $S_1$. In this position, the head 697 of the rocker 650 is received at least partially within the first recess 662 of the first hinge member 660, releasing the bending force on the arm 698. In this position the head 697 is free to move between the two recesses 662 and 663. As the second hinge member 261 begins to rotate about the second axis of rotation $A_2$, the cam shape of the surface 671 forces the head 697 of the rocker 650 into the first recess 662 of the first hinge member 660, effectively jamming and precluding rotation of the first hinge member 660 about the first axis of rotation $A_1$.

Referring to FIG. 7C, the second hinge member 661 has pivoted about the second axis of rotation $A_2$ to a position where the pin 253 is at the second endpoint 227 of the slot 222 in the back plate 200. The second hinge member 661 accordingly cannot pivot further about the second axis of rotation $A_2$ in the direction $S_2$. Throughout the rotation of the second hinge member 661 from the position in FIG. 7B to the position in FIG. 7C, the head 697 of the rocker 650 remains in the first recess 662 of the first hinge member 660 precluding the first hinge member 660 from pivoting about the first axis of rotation $A_1$. Because the head 697 of the rocker 650 is at least partially within the first recess 662 of the first hinge member 660, the first hinge member 660 requires a greater force to rotate in a direction $S_3$ than the force required for the second hinge member 661 to rotate in a direction $S_4$. Accordingly, the rocker 650 encourages the second hinge member 661 to pivot in the direction $S_4$ about the second axis of rotation $A_2$ before the first hinge member 660 pivots in the direction $S_3$ about the first axis of rotation $A_1$. In additional embodiments, the hinge 710 can have a rocker with a different configuration, or the hinge may not have a rocker. Furthermore, FIGS. 7A–7C illustrate the full range of extension (FIGS. 7A–B) and flexion (FIGS. 7B–C) of the illustrated embodiment. Other embodiments can also have this range of extension and flexion without the rocker 650 or other components.

Figure 8:
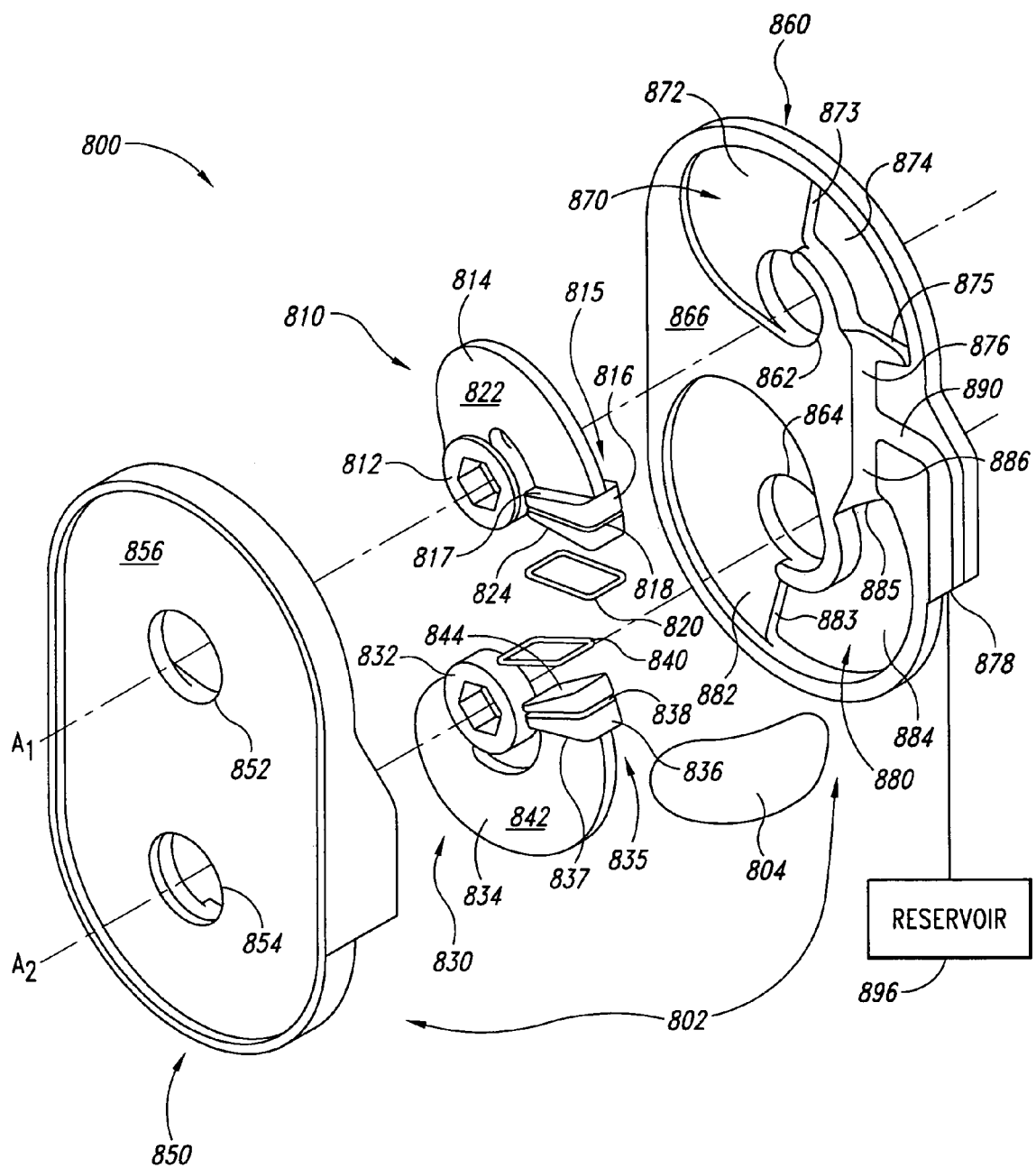
FIG. 8 is an isometric exploded view of a power pack in accordance with one embodiment of the invention.

FIG. 8 is an isometric exploded view of a power pack 800 in accordance with one embodiment of the invention that can be used with embodiments of the hinges 10 and 710 described above, and also with other types of single axis or bicentric hinges. In the illustrated embodiment, the power pack 800 includes a first piston 810, a second piston 830, and a housing 802 having a front portion 850 and a rear portion 860. The first piston 810 in the embodiment shown in FIG. 8 is a rotary piston that is received within an upper cavity 870 in a front side 866 of the rear portion 860 of the housing 802, and a similar cavity (not shown) in the backside (not shown) of the front portion 850 of the housing 802. Similarly, the second piston 830 in the embodiment shown in FIG. 8 is a rotary piston that is received within a lower cavity 880 in the front side 866 of the rear portion 860 of the housing 802 and a similar cavity (not shown) in the backside (not shown) of the front portion 850 of the housing 802. In other embodiments, the pistons can be linear pistons, and a portion of the pistons can extend outside the housing 802.

The first piston 810 of the illustrated embodiment includes a hub 812, an arm 814 attached to the hub 812, and a head 816 attached to a distal portion 815 of the arm 814. A portion of the hub 812 projects beyond a back surface (not shown) of the arm 814 and is received within an aperture 862 in the rear portion 860 of the housing 802. Another portion of the hub 812 projects beyond a front surface 822 of the arm 814 and is received within an aperture 852 in the front portion 850 of the housing 802. The apertures 852 and 862 and the hub 812 are aligned with the first axis of rotation $A_1$ about which the first piston 810 rotates. The arm 814 of the first piston 810 is received within a channel 872 in the upper cavity 870 of the housing 802. The channel 872 is sized and configured to permit the arm 814 to pivot about the first axis of rotation $A_1$. The head 816 of the piston 810 is received within an annular chamber 874 in the upper cavity 870 of the housing 802 in this embodiment. The annular chamber 874 is sized and configured to permit the head 816 to pivot about the first axis of rotation $A_1$. As the first piston 810 rotates about the first axis of rotation $A_1$, the head 816 moves through the annular chamber 874 from a position in which a surface 817 on the head 816 contacts a first wall 873 in the chamber 874 to a position in which a top surface 824 on the head 816 contacts a second wall 875 in the chamber 874. Thus, the first wall 873 and the second wall 875 of the chamber 874 define the stops for the first piston 810.

The second piston 830 of the illustrated embodiment includes a hub 832, an arm 834 attached to the hub 832, and a head 836 attached to a distal portion 835 of the arm 834. A portion of the hub 832 projects beyond a back surface (not shown) of the arm 834 and is received within an aperture 864 in the rear portion 860 of the housing 802. Another portion of the hub 832 projects beyond a front surface 842 of the arm 834 and is received within an aperture 854 in the front portion 850 of the housing 802. The apertures 854 and 864 and the hub 832 are aligned with the second axis of rotation $A_2$ about which the second piston 830 rotates. The arm 834 of the second piston 830 is received within a channel 882 in the lower cavity 880 of the housing 802. The channel 882 is sized and configured to permit the arm 834 to pivot about the second axis of rotation $A_2$. The head 836 of the second piston 830 is received within an annular chamber 884 in the lower cavity 880 of the housing 802 in this embodiment. The annular chamber 884 is sized and configured to permit the head 836 to pivot about the second axis of rotation $A_2$. As the second piston 830 rotates about the second axis of rotation $A_2$, the head 836 moves through the annular chamber 884 from a position in which a surface 837 on the head 836 contacts a first wall 883 in the chamber 884 to a position in which a top surface 844 on the head 836 contacts a second wall 885 in the chamber 884. Thus, the first wall 883 and the second wall 885 of the chamber 884 define the stops for the second piston 830.

In the illustrated embodiment, the first and second pistons 810 and 830 are the same size and shape. In additional embodiments, the pistons 810 and 830 can be shaped or configured differently. For example, one piston can have an annular arm with a greater radius than the arm of the other piston, or one piston can have a head with a different size or shape than the head of the other piston. In still other embodiments, the power pack can have only one piston. In the illustrated embodiment, the annular chamber 884 in the upper cavity 870 has a longer arc length than the annular chamber 874 in the lower cavity 880, and the upper annular channel 882 is bigger than the lower annular channel 872. These differences in size allow the second piston 830 to pivot further about the second axis of rotation $A_2$ than the first piston can pivot about the first axis of rotation $A_1$. In additional embodiments, the range of pivot and the size of the channels and chambers can be the same. Or alternatively, the first piston 810 can have a greater range of pivot than the second piston 830. In additional embodiments, the housing may not have a channel, or the channel and chamber can be shaped or configured differently. For example, the chamber can be linear rather than annular.

The annular chamber 874 of the upper cavity 870 is configured to receive and hold a fluid (not shown). In one embodiment, the fluid is a mineral oil; in other embodiments, water or hydraulic fluids can be used. The fluid is displaced from the chamber 874 into an upper fluid passageway 876 as the head 816 moves through the annular chamber 874 when the first piston 810 rotates about the first axis of rotation $A_1$. The fluid flows from the upper fluid passageway 876 through a side fluid passageway 890 to an outlet 878 that is coupled to a reservoir 896. Similarly, the annular chamber 884 of the lower cavity 880 is configured to receive and hold the fluid. In the illustrated embodiment, the annular chamber 884 includes a rolling bladder 804. In other embodiments, both annular chambers can include a sleeve or a bladder, or the chambers may not include either. In the illustrated embodiment, the fluid is displaced from the chamber 884 into a lower fluid passageway 886 as the head 836 moves through the annular chamber 884 when the second piston rotates 830 about the second axis of rotation $A_2$. The fluid flows from the lower fluid passageway 886 through the side fluid passageway 890 to the outlet 878. In additional embodiments, the upper fluid passageway 876 and the lower fluid passageway 886 can remain separate, and each passageway 876 and 886 can have a separate outlet and reservoir.

In the illustrated embodiment, the heads 816 and 836 of the first and second pistons 810 and 830 have rectangular cross-sectional shapes to provide more surface area in the small space within the housing 802. Furthermore, in the illustrated embodiment, the heads 816 and 836 have grooves 818 and 838 to receive seals 820 and 840. The seals 820 and 840 prevent fluid from leaking into the channels 872 and 884. In additional embodiment, the heads 816 and 836 can have different cross-sectional shapes such as a circular shape. In other embodiments, the heads 816 and 836 may not have seals or may have different seals.

Figure 9:
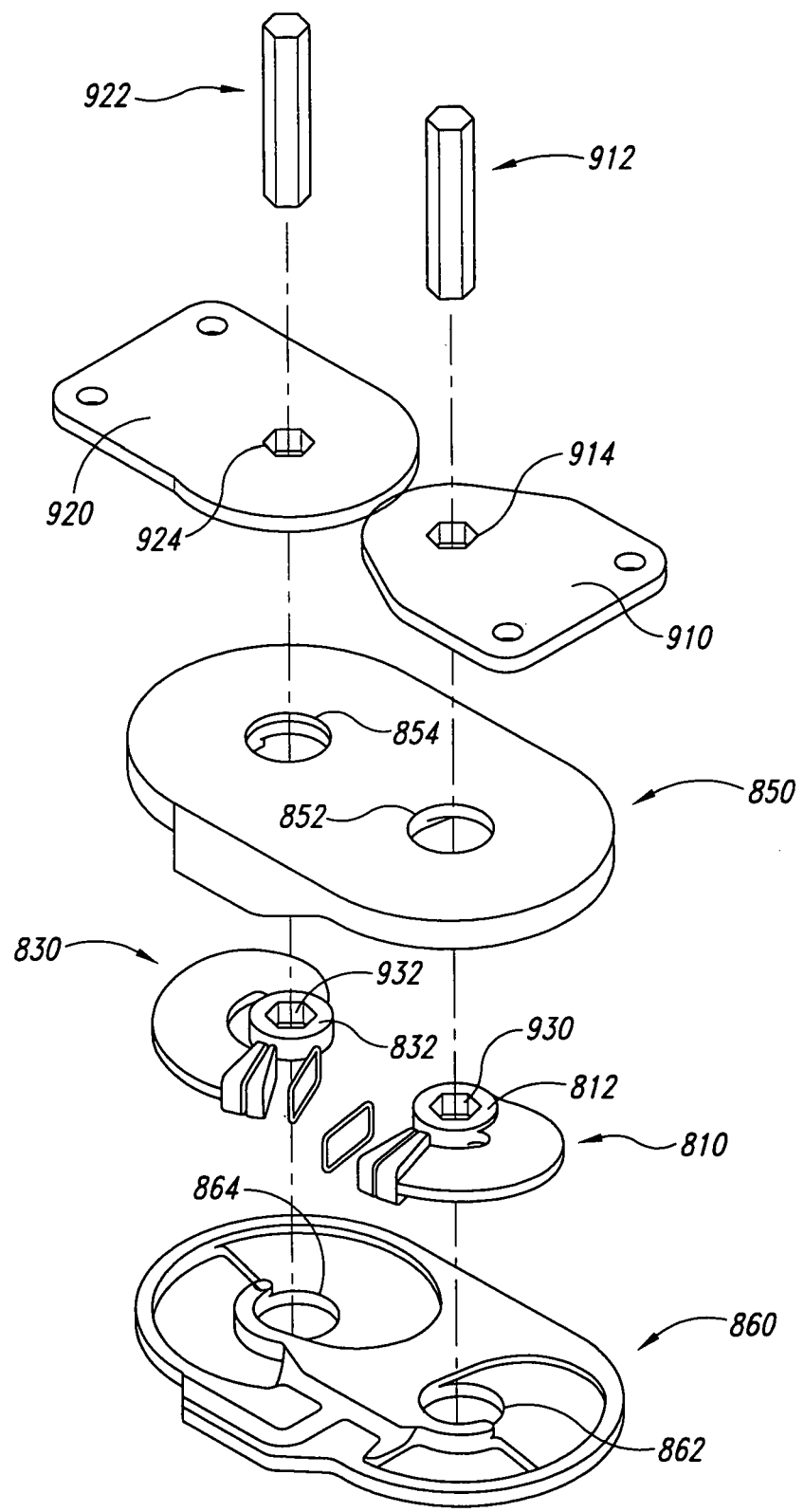
FIG. 9 is an isometric exploded view of a hinge having a power pack, a first hinge member, and a second hinge member in accordance with one embodiment of the invention.

FIG. 9 is an isometric exploded view of the connection between the power pack 800, a first hinge member 910, and a second hinge member 920 in accordance with one embodiment of the invention. The first hinge member 910 and the second hinge member 920 can be used in the hinges 10 and 710 described above, or they can be used in different bicentric hinges (including geared or non-geared hinges). In the illustrated embodiment, a first rod 912 couples the first hinge member 910 to the hub 812 of the first piston 810. The first rod 912 is received within an aperture 914 in the first hinge member 910 and an aperture 930 in the hub 812 of the first piston 810. Similarly, a second rod 922 couples the second hinge member 920 to the hub 832 of the second piston 830. The second rod 922 is received within an aperture 924 in the second hinge member 920 and an aperture 932 in the hub 832 of the second piston 830. In the illustrated embodiment, the rods 912 and 922 and the apertures 914, 924, 930 and 932 are hexagonal so that the rods 912 and 922 translate rotation of the hinge members 910 and 920 to the pistons 810 and 830. In other embodiments, the pistons 810 and 830 can be coupled to the hinge members 910 and 920 by other methods. For example, the pistons, rods, and hinge member can be rotatably coupled with a keyway-spline connection.

Figure 10A:
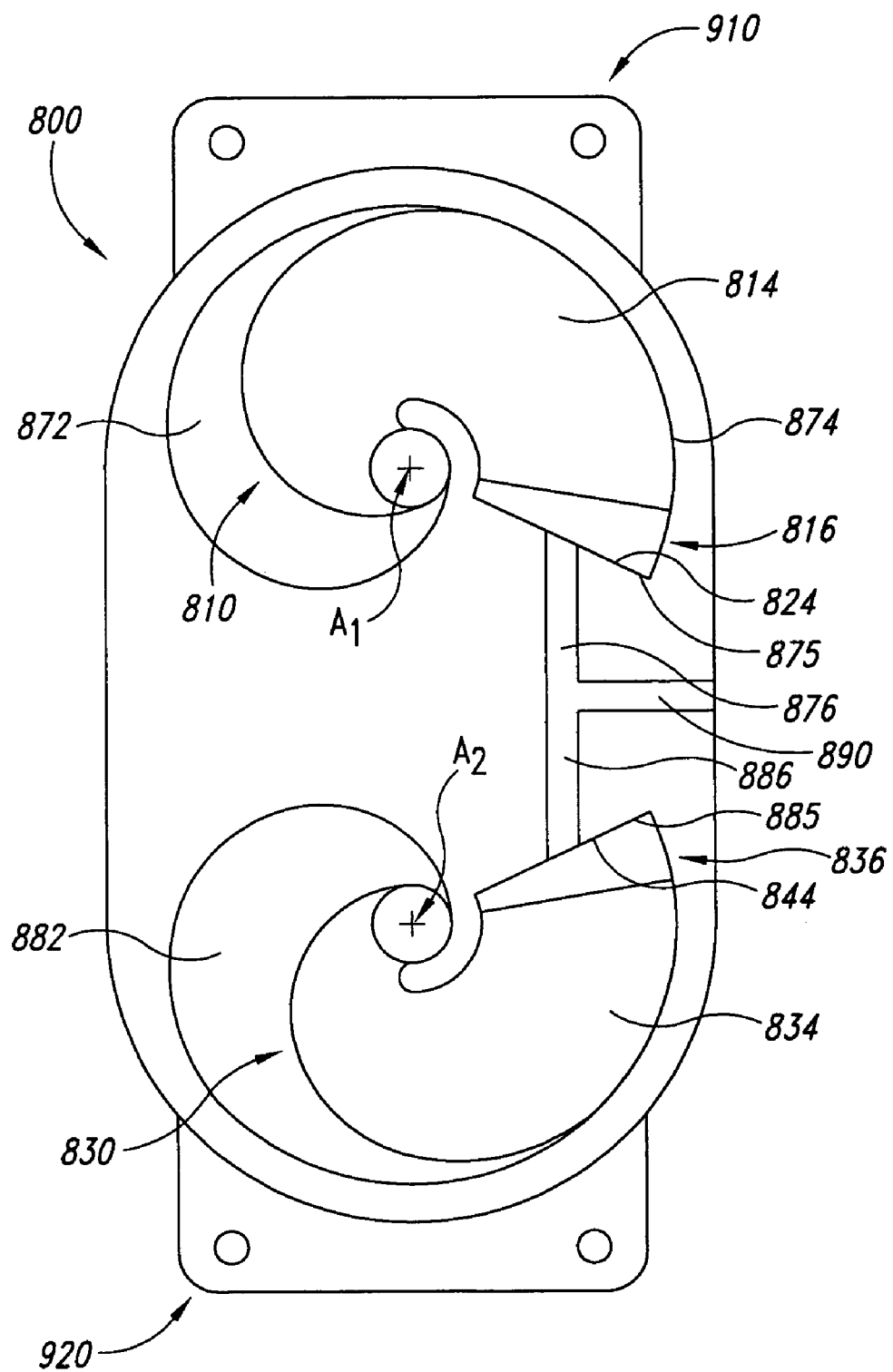
FIGS. 10A–10C are top plan views of a power pack attached to a first hinge member and a second hinge member in accordance with another embodiment of the invention.
Figure 10B:
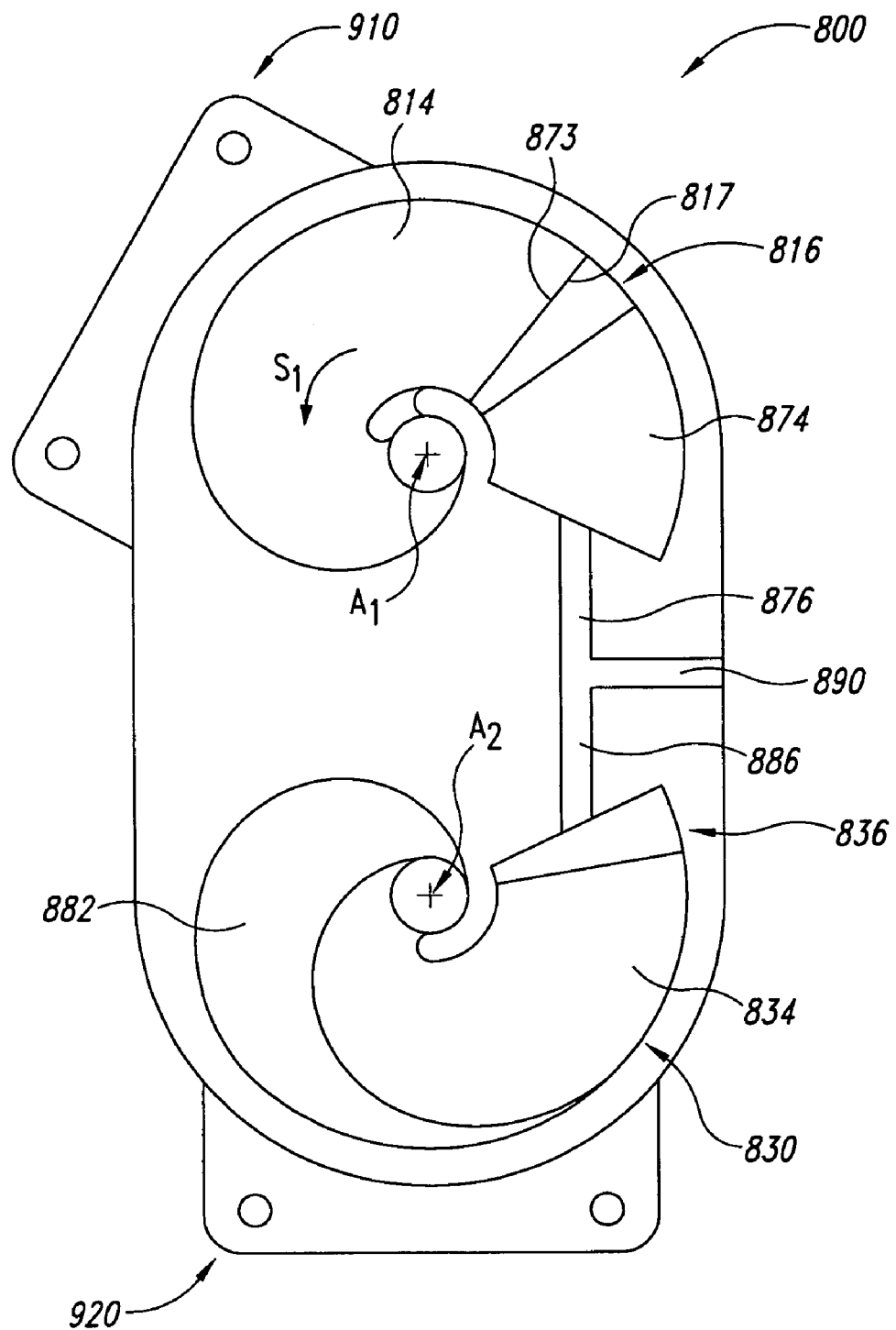
Figure 10C:
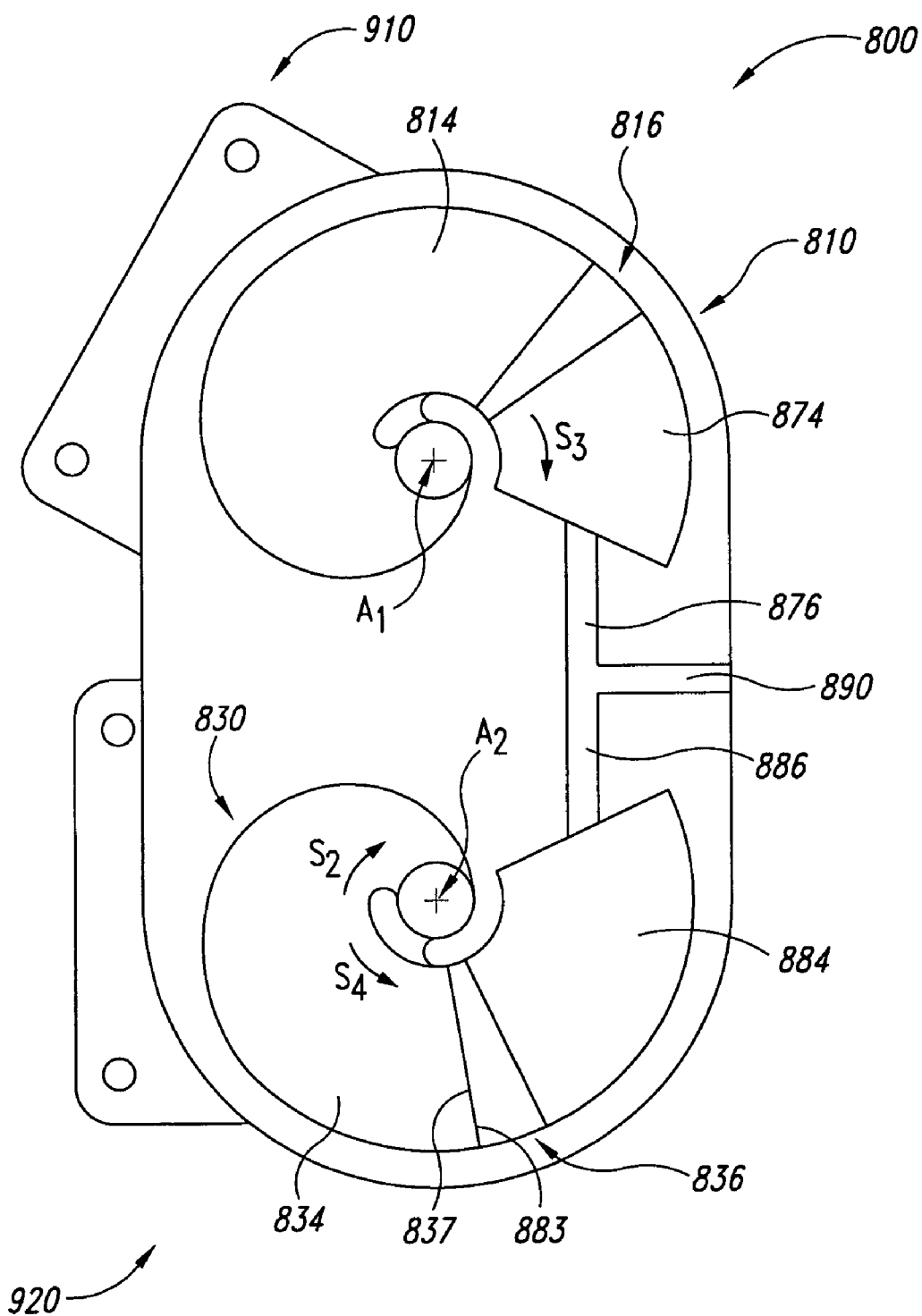

FIGS. 10A–10C are top plan views of the power pack 800 attached to the first hinge member 910 and the second hinge member 920. FIG. 10A illustrates the power pack 800 when the first and second hinge members 910 and 920 are in the full-extension position (i.e., corresponding to full leg extension). The first piston 810 is accordingly positioned so that the top surface 824 of the head 816 contacts the second wall 875 of the chamber 874. The second piston 830 is similarly positioned so that the top surface 844 of the head 836 contacts the second wall 885 of the chamber 884. As a result, the fluid is displaced from the chambers 874 and 884 when the hinge members 910 and 920 are in the full-extension position.

FIG. 10B illustrates the power pack 800 when the first and second hinge members 910 and 920 are in an intermediate position between full-extension and full-flexion. The rotation of the first hinge member 910 in the direction $S_1$ about the first axis of rotation $A_1$ moves the first piston 810 from the position illustrated in FIG. 10A to the position illustrated in FIG. 10B. As the first piston 810 rotates, the head 816 moves through the annular chamber 874 drawing the fluid into the chamber 874 from the upper fluid passageway 876. The first piston 810 continues to rotate until the surface 817 of the head 816 contacts the first wall 873 of the chamber 874. The first wall 873 of the chamber 874 precludes further rotation of the first piston 810, and consequently the first hinge member 910, about the first axis of rotation $A_1$ in the direction $S_1$.

FIG. 10C illustrates the power pack 800 when the first and second hinges 910 and 920 are in the full-flexion position. The rotation of the second hinge member 920 in the direction $S_2$ about the second axis of rotation $A_2$ moves the second piston 830 from the position illustrated in FIG. 10B to the position illustrated in FIG. 10C. As the second piston 830 rotates, the head 836 moves through the annular chamber 884 drawing the fluid into the chamber 884 from the lower fluid passageway 886. In other embodiments, the second piston 830 can rotate before the first piston 810 rotates. Referring to FIG. 10C, the second piston 830 is illustrated in a position with the surface 837 of the head 836 contacting the first wall 883 in the lower annular chamber 884. The first wall 883 of the chamber 884 precludes further rotation of the second piston 830, and consequently the second hinge member 920, about the second axis of rotation $A_2$ in the direction $S_2$. From the position illustrated in FIG. 10C the first piston 810 can displace the fluid from the chamber 874 by rotating about the first axis of rotation $A_1$ in the direction $S_3$ to the position illustrated in FIG. 10A. Similarly, the second piston 830 and the second hinge member 920 can displace the fluid from the chamber 884 by rotating about the second axis of rotation $A_2$ in the direction $S_4$ to the position illustrated in FIG. 10A.

Figure 11:
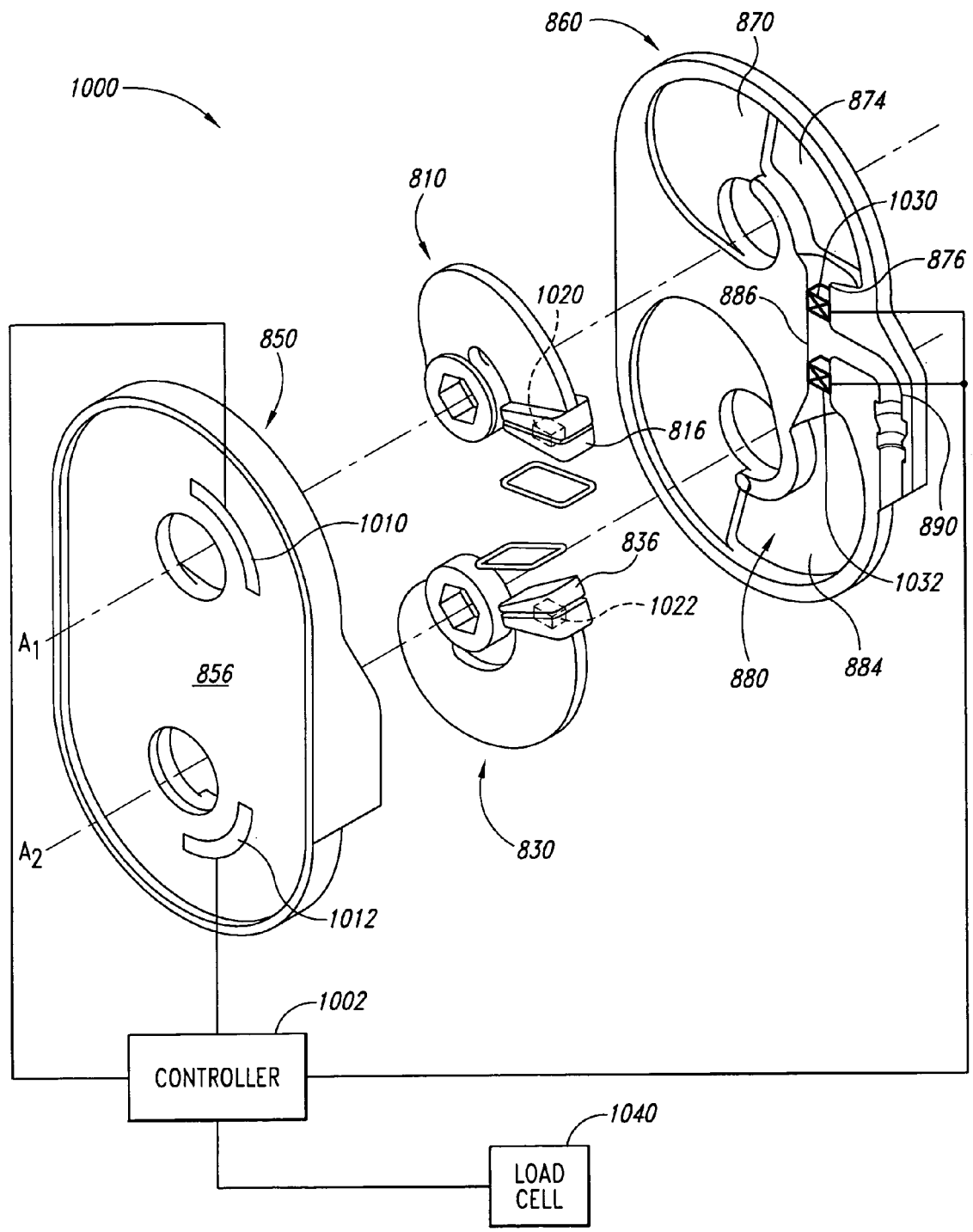
FIG. 11 is an isometric exploded view of a power pack having valves to control the fluid flow in accordance with another embodiment of the invention.

FIG. 11 is an isometric exploded view of a power pack 1000 having valves 1030 and 1032 to control the fluid flow in accordance with another embodiment of the invention. The power pack 1000 is similar to the power pack 800 described above, and like reference numbers refer to like components in FIGS. 8–11. The power pack 1000 of the illustrated embodiment has a first valve 1030 in the upper fluid passageway 876 and a second valve 1032 in the lower fluid passageway 886. The valves 1030 and 1032 control the fluid flow through the respective fluid passageways 876 and 886. When the upper valve 876 is partially closed, the fluid flow through the upper fluid passageway 876 is restricted, and consequently, the head 816 of the first piston 810 moves at a reduced speed within the chamber 874. When the upper valve 876 is closed, no fluid can flow through the upper fluid passageway 876, and consequently, the head 816 of the first piston 810 cannot move within the chamber 874. Accordingly, the valves 1030 and 1032 can control the ability of the pistons 810 and 830, and therefore the hinge members 910 and 920 (FIG. 9), to rotate about the first and second axes of rotation $A_1$ and $A_2$. Furthermore, the valves 1030 and 1032 can control the speed at which the hinge members 910 and 920 rotate. In one embodiment, the valves 1030 and 1032 can be piezoelectric valves. In another embodiment, the power pack 1000 can have other valves or only one valve.

In the illustrated embodiment, the valves 1030 and 1032 are controlled by a controller 1002. The controller 1002 can be a programmable chip with memory that is mounted on or in the housing 802. The controller 1002 can be programmed using a separate hand-set with an infrared link or a hard-wired link. The controller 1002 can communicate with the valves 1030 and 1032 through a wired, wireless, or infrared connection. Thus, as explained below, the controller 1002 can control the rotation of the first and second hinge members 910 and 920 by restricting or stopping the flow of fluid through the valves 1030 and 1032.

In the illustrated embodiment, the power pack 1000 contains a system to automatically adjust the valves 1030 and 1032 to a particular setting corresponding to the position of the heads 816 and 836 in the chambers 874 and 834. The system includes a first magnet 1020 disposed in the head 816 of the first piston 810 and a second magnet 1022 disposed in the head 836 of the second piston 830. The front portion 850 of the housing 802 contains magnetic strips 1010 and 1012 positioned adjacent to the chambers 874 and 884. The magnetic strips 1010 and 1012 sense the location of the magnets 1020 and 1022, and consequently the position of the heads 816 and 836. The magnetic strips 1010 and 1012 can communicate with the controller 1002 through a wired, wireless, or infrared connection. Accordingly, the valves 1030 and 1032 can be adjusted to a particular setting corresponding to the position of the heads 816 and 836. In other embodiments, other position sensing devices can be used.

The ability to adjust the valves 1030 and 1032 depending on the location of the heads 816 and 836 allows the power pack 1000 to slow the pistons 810 and 830 and the first and second hinge members 910 and 920 before they reach the range of motion stops. For example, if a user is participating in a vigorous activity such as skiing, the power pack 1000 can slow the rotation of the hinge members 910 and 920, and accordingly the movement of the knee joint, before the hinge members 910 and 920 reach the range of motion stops. In other embodiments, the power pack 1000 can slow the rotation of the hinge members 910 and 920 when a user begins rotating the hinge members 910 and 920 at a speed that could result in a knee injury. Braking or slowing the hinge members 910 and 920 before the rotation stops can reduce the high loads in the knee joint and the knee brace caused by abrupt stops. Moreover, braking can reduce the risk of hyperextension in the knee joint. Furthermore, the ability to adjust the valves 1030 and 1032 based on a corresponding position of the heads 816 and 836 also allows a user to have flexibility in setting the range of motion limitations. For example, the controller 1002 can be programmed to allow for a greater range of motion during the time of day that a user has therapy, and a limited range of motion during the time of day that the user exercises.

In the illustrated embodiment, a load cell 1040 is operatively coupled to the controller 1002. The load cell 1040 can be used to trigger the controller 1002 to restrict rotation of one or both of the pistons 810 and 830 when the load cell 1040 is loaded. For example, the load cell 1040 can be placed in a shoe (not shown). In this particular embodiment, the load cell 1040 can trigger the controller 1002 to restrict rotation of the first and second pistons 810 and 830 when the shoe is subjected to a load. This embodiment could be useful, for example, for people who have lost the function of their quadriceps or have polio. In one embodiment, the load cell 1040 triggers the controller 1002 to restrict rotation of the first and second hinge members 910 and 920 at heal strike, allowing a person to put weight on the leg without concern of the knee bending. Once the toe is off the ground, the load cell 1040 triggers the controller 1002 to permit rotation of the first and second hinge members 910 and 920 so that the leg can be rotated forward. In other embodiments, the load cell 1040 can be positioned proximate a muscle in the body. Accordingly, the tension of the muscle can trigger the load cell 1040 to allow or restrict rotation of the hinge members 910 and 920. In additional embodiments, the load cell 1040 can be positioned in other locations.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

I claim:

1. A hydraulic power pack for use with a bicentric hinge having a first hinge member that rotates about a first axis and a second hinge member that rotates about a second axis, the power pack comprising:
   a housing having a cavity, the housing having an attachment mechanism configured to attach the housing to the hinge; and
   a rotary piston disposed at least partially within the cavity, the rotary piston having a head and an arm configured to be connected to the head and one of the hinge members, the head being moveable about the first axis along a circular path through the cavity.

2. The power pack of claim 1 wherein the cavity includes a chamber and an annular channel, and the head is moveable within the chamber between a first position and a second position.

3. The power pack of claim 1 wherein the housing includes a fluid passageway that is in fluid communication with the cavity.

4. The power pack of claim 1, further comprising a bladder disposed within the cavity.

5. The power pack of claim 1 wherein the rotary piston includes an engagement member connected to the arm, the engagement member configured to be engaged by one of the hinge members of the hinge.

6. The power pack of claim 1 wherein the head has a generally rectangular cross-sectional shape.

7. The power pack of claim 1 wherein the cavity includes a chamber and a channel, the head is moveable within the chamber between a first position and a second position, and the housing includes a fluid passageway in fluid communication with the chamber.

8. The power pack of claim 1 wherein the housing includes a fluid passageway in fluid communication with the cavity, the power pack further comprising:
   a valve to selectively restrict fluid flow through the fluid passageway.

9. The power pack of claim 1 wherein the housing includes a fluid passageway in fluid communication with the cavity, the power pack further comprising:
   a piezoelectric valve to selectively restrict fluid flow through the fluid passageway.

10. The power pack of claim 1, further comprising:
    a duct in fluid communication with the cavity; and
    a reservoir to receive a fluid displaced from the cavity, the reservoir being in fluid communication with the duct.

11. The power pack of claim 1 wherein the head includes a magnet, the housing includes a magnetic strip to sense the location of the magnet and a fluid passageway in fluid communication with the cavity, the power pack further comprising:
    a valve to selectively restrict fluid flow through the fluid passageway; and a controller operatively coupled to the magnetic strip and the valve so that the controller can adjust the valve depending on the position of the head.

12. The power pack of claim 1 wherein the head includes a position sensor, the housing includes a fluid passageway in fluid communication with the cavity, the power pack further comprising:
   a valve to selectively restrict fluid flow through the fluid passageway; and
   a controller operatively coupled to the position sensor and the valve so that the controller can adjust the valve depending on the position of the head.

13. The power pack of claim 1 wherein the housing includes a fluid passageway that is in fluid communication with the cavity, the power pack further comprising:
   a valve to selectively restrict fluid flow through the fluid passageway;
   a load sensor; and
   a controller operatively coupled to the load sensor and the valve so that the controller can adjust the valve when the load sensor experiences a load.

14. A hinge with a power pack for use in a brace having a frame, the apparatus comprising:
   a plate;
   a first member pivotally attached to the plate, the first member being pivotable about a first axis of rotation;
   a second member pivotally attached to the plate, the second member being pivotable about a second axis of rotation, the second axis of rotation being spaced apart from the first axis of rotation; and
   a power pack, including:
      a housing having a cavity and an attachment mechanism configured to attach the housing to the hinge; and
      a rotary piston disposed at least partially within the cavity, the rotary piston having a head and an arm configured to be coupled to the head and one of the first and second members, the head being moveable about the first axis along a circular path in the cavity.

15. The apparatus of claim 14 wherein the cavity includes a chamber and a channel, the head is moveable within the chamber between a first position and a second position, and the housing includes a fluid passageway in fluid communication with the chamber.

16. The apparatus of claim 14 wherein the housing includes a fluid passageway in fluid communication with the cavity, the power pack further comprising:
   a valve to selectively restrict fluid flow through the fluid passageway.

17. A method for controlling the speed of a hinge, comprising:
   pivoting a hinge member coupled to a rotary piston about an axis of rotation from a first position to a second position at a first speed;
   displacing a fluid from a cavity to a fluid passageway as the rotary piston pivots;
   adjusting a valve to change a flow of the fluid displaced by the rotary piston; and
   rotating the hinge member from the second position to a third position about the first axis of rotation at a second speed different from the first speed.

18. The method of claim 17, further comprising slowing the movement of the hinge member.

19. The method of claim 17, further comprising sensing a position of the hinge member as it moves; and
   wherein adjusting a valve to change the flow includes adjusting the valve to a particular setting corresponding to the position of the hinge member.

20. A method for controlling the speed of a hinge, comprising:
   pivoting a hinge member coupled to a rotary piston about an axis of rotation from a first position to a second position at a first speed;
   drawing a fluid from a fluid passageway into a cavity as the rotary piston pivots;
   adjusting a valve to change a flow of the fluid drawn by the rotary piston; and
   rotating the hinge member from the second position to a third position about the first axis of rotation at a second speed different from the first speed.

21. A method for stopping the rotation of a hinge, comprising:
   pivoting a hinge member coupled to a rotary piston about an axis of rotation from a first position to a second position;
   displacing a fluid from a cavity to a fluid passageway as the rotary piston rotates; and
   precluding rotation of the rotary piston and the hinge member about the axis of rotation by restricting the flow of the fluid displaced by the rotary piston.

22. A method for stopping the rotation of a hinge, comprising:
   pivoting a hinge member coupled to a rotary piston about an axis of rotation from a first position to a second position;
   drawing a fluid from a fluid passageway into a cavity as the rotary piston rotates; and
   precluding rotation of the rotary piston and the hinge member about the axis of rotation by restricting the flow of the fluid drawn by the rotary piston.

* * * * *